United States Patent
Plata-Salaman et al.

(10) Patent No.: US 7,078,436 B2
(45) Date of Patent: Jul. 18, 2006

(54) CARBAMATE COMPOUNDS FOR USE IN PREVENTING OR TREATING ANXIETY DISORDERS

(75) Inventors: Carlos R. Plata-Salaman, Ambler, PA (US); Boyu Zhao, Lansdale, PA (US); Roy E. Twyman, Doylestown, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 93 days.

(21) Appl. No.: 10/081,713

(22) Filed: Feb. 21, 2002

(65) Prior Publication Data

US 2002/0143053 A1 Oct. 3, 2002

Related U.S. Application Data

(60) Provisional application No. 60/271,689, filed on Feb. 27, 2001.

(51) Int. Cl.
A61K 31/27 (2006.01)

(52) U.S. Cl. .......................... 514/483; 514/488; 514/489
(58) Field of Classification Search ................ 514/483, 514/488, 489
See application file for complete search history.

(56) References Cited

U.S. PATENT DOCUMENTS

| | | | |
|---|---|---|---|
| 3,248,418 A | 4/1966 | Bossinger et al. | |
| 3,265,728 A | 8/1966 | Bossinger et al. | |
| 3,278,380 A | 10/1966 | Bossinger et al. | |
| 3,313,692 A | 1/1967 | Bossinger et al. | |
| 5,698,588 A | * 12/1997 | Choi et al. | |
| 6,103,759 A | 8/2000 | Choi et al. | |
| 6,541,513 B1 | 4/2003 | Plata-Salaman et al. | .... 514/483 |
| 6,562,867 B1 | 5/2003 | Plata-Salaman et al. | .... 514/489 |

OTHER PUBLICATIONS

Stein, M.B., *Neurobiological Perspectives on Social Phobia*: From Affiliation to Zoology, Biol. Psychiatry, 1998, 4 (12), 1277–1285.

Newburn, G., *Psychiatric Disorders Associated with Traumatic Brain Injury*, Optimal Treatment, CNS Drugs, 1998, ( 6), 441–445.

Lipper, S. et al., *Preliminary Study of Carbamazepine in Post–Traumatic Stress Disorder*, Ppsychosomatics, 1986, 27 ( 12) 849–854.

Looff, D., et al., *Carbamazepine for PTSD*, J. Am. Acad. Child Adolesc. Psychiatry, 1995, 34 (6), 703–704.

MacLeod, A.D., *Vigabatrin and Posttraumatic Stress Disorder*, J. Clin. Psychopharmacol, 1996, 16(2), 190–191.

Szymanski, H.V., et al., *Divalproex in Posttraumatic Stress Disorder*, Am. J. Psychiatry, 1991, 148 (8) 1086–1087.

Marion W. Wolf, Afshin Alavi, Aron D. Mosnaim, Posttraumatic Stress Disorder in Vietnam Veterans Clinical and EEG Findings, Possible Therapeutic Effect of Carbamazepine, Biol Psychiatry, 1988;23:642–644.

* cited by examiner

Primary Examiner—Phyllis G. Spivack
(74) Attorney, Agent, or Firm—Peter L. Herridge

(57) ABSTRACT

This invention is directed to a method for preventing or treating anxiety disorders comprising administering to a subject in need thereof a therapeutically effective amount of a compound selected from the group consisting of Formula (I) and Formula (II):

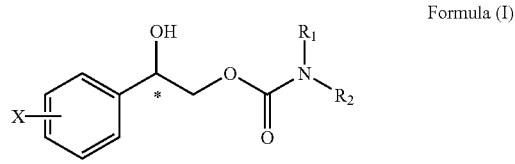

Formula (I)

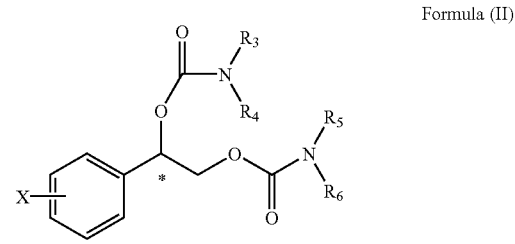

Formula (II)

wherein phenyl is substituted at X with one to five halogen atoms selected from the group consisting of fluorine, chlorine, bromine and iodine; and, $R_1$, $R_2$, $R_3$, $R_4$, $R_5$ and $R_6$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

22 Claims, No Drawings

CARBAMATE COMPOUNDS FOR USE IN PREVENTING OR TREATING ANXIETY DISORDERS

CROSS REFERENCE TO RELATED APPLICATIONS

This application claims benefit of provisional application Ser. No. 60/271,689, filed Feb. 27, 2001, which is hereby incorporated by reference.

FIELD OF THE INVENTION

This invention is directed to a method for use of a carbamate compound in preventing or treating anxiety disorders. More particularly, this invention is directed to a method for use of halogenated 2-phenyl-1,2-ethanediol monocarbamate or dicarbamate compounds for preventing or treating anxiety disorders.

BACKGROUND OF THE INVENTION

Anxiety disorders, one of the most prevalent psychiatric illnesses in the general community, represents a group of emotional states consisting of psychophysiological responses to anticipation of unreal or imagined danger which are not a result of physical disorders, drug abuse or other psychiatric conditions (Anxiety Overview, *Market Research Reports,* 2001; Briley M and Moret C, Present and Future Anxiolytics, *Drugs,* 2000, 3 (7), 695–699; Stein M B, Neurobiological perspectives on social phobia: From affiliation to zoology, *Biol. Psychiatry,* 1998, 44 (12), 1277–1285; Newburn G, Psychiatric disorders associated with traumatic brain injury. Optimal treatment, *CNS Drugs,* 1998, 9 (6), 441–456; Lidberg L, et. al., Suicide attempts and impulse control disorder are related to low cerebrospinal fluid 5-HIAA in mentally disordered violent offenders, *Acta Psychiatr. Scand.,* 2000, 101 (5), 395–402; Van Ameringen M, et. al., Drugs in development for social anxiety disorder: more to social anxiety than meets the SSRI, *Expert Opin. Invest. Drugs,* 2000, 9 (10), 2215–2231; Zhuang X, et. al., Altered emotional states in knockout mice lacking 5-HT1A or 5-HT1B receptors, *Neuropsychopharmacology,* 1999, 21 (2S), 52S–60S).

Anxiety disorders include, but are not limited to, generalized anxiety disorders, panic disorders (including those with or without agoraphobia and symptoms of anticipatory anxiety, recurrent sleep panic attacks (not nightmares) and distressing symptoms (eg, dyspnea, tachycardia, palpitations, headaches, dizziness, paresthesias, choking, smothering feeling, nausea and bloating) in association with feelings of impending doom (i.e., an alarm response)), impulse control disorders (such as obsessive-compulsive disorder (OCD), bulimia, episodic dyscontrol, trichotillomania, compulsive gambling and kleptomania), phobic disorders (those disorders with feelings of displacement not due to impaired cognitive abilities (social phobia and avoidant personality disorders, including both global social phobia and specific social phobia, simple phobia, agoraphobia, apiphobia, tropophobia, astrapophobia, triskaidekaphobia, blennophobia, thalassophobia, claustrophobia, spheksophobia, cynophobia, sciophobia, decidophobia, eletrophobia, scholionophobia, eremophobia, pyrophobia, gamophobia, pnigerophobia, ophidiophobia, odynophobia, nyctophobia, ochlophobia, musophobia, keraunophobia, katagelophobia, kakorraphiophobia, hydrophobia, gynophobia, gatophobia, gephyrophobia, acrophobia or amathophobia)), posttraumatic stress disorder (PTSD), dissociative states (including amnesia, somnambulism, dissociative identity disorder or depersonalization), presurgical anxiety states, postsurgical anxiety states or other medical or psychiatric induced anxiety conditions (including, but not limited to, anxiety resulting from traumatic brain injury, chronic pain disorders or other chronic disease conditions).

OCD is one of the most common psychiatric disorders, occurring in 2–3% of the U.S. population. In OCD, the irrational idea or the impulse persistently intrudes into awareness with obsessions (constantly recurring thoughts) and compulsions (repetitive actions). Since dysfunctions of the serotonergic system have been particularly implicated in OCD, traditional pharmacological interventions have included SSRIs (selective serotonin reuptake inhibitors), clomipramine, MAOIs (monoamine oxidase inhibitors) and clonazepam. Approximately 60% of OCD patients respond to serotonergic drugs in doses equivalent to those used for depression such as sertraline, paroxetine, fluvoxamine and buspirone. In addition, there is clinical evidence that epilepsy and OCD are associated disorders on the basis that the abnormal neuronal firing present in both disorders can be regulated by anticonvulsants with a broad spectrum of activity. For example, OCD patients, even those with refractory OCD, showed clinical improvement after treatment with anticonvulsant drugs such as carbamazepine and gabapentin (Iwata Y, et. al., Carbamazepine augmentation of clomipramine in the treatment of refractory obsessive-compulsive disorder [letter], *J. Clinical Psychiatry,* 2000, 61 (7), 528–529; Hollander E, Managing aggressive behavior in patients with obsessive-compulsive disorder and borderline personality disorder, *J. Clinical Psychiatry,* 1999, 60 (Suppl), 1538–1544; Cora-Locatelli G, et. al., Gabapentin augmentation for fluoxetine-treated patients with obsessive-compulsive disorder [lefter], *J. Clinical Psychiatry,* 1998, 59 (9), 480–481; Koopowitz L F and Berk M, Response of obsessive compulsive disorder to carbamazepine in two patients with comorbid epilepsy, *Annals of Clinical Psychiatry,* 1997, 9 (3), 171–173).

According to the recent National Comorbidity Study (Anxiety Overview, Market Research Reports, 2001), social phobia (both global and specific) occurs in 13.3% of the population, one of the highest among anxiety disorders and the most misunderstood. Social phobia, if left untreated, will become associated with extensive morbidity and disability, leading to lifelong impairment in social development and occupational functioning. In global social phobia, all social situations are poorly tolerated, while specific social phobia includes performance anxiety or well-delineated phobia. Although the primary intervention for social phobia is environmental, pharmacological interventions have been shown to be effective in the treatment of social phobia. MAOIs can be effective in the treatment of social phobia, but it is unclear whether their effect arises from a primary effect on social phobia or from improved attention ability allowing for a better coping response. Central serotonergic dysregulation and abnormalities in dopaminergic function are believed to be associated with social phobia (Stein M B, Neurobiological perspectives on social phobia: From affiliation to zoology, *Biol. Psychiatry,* 1998, 44 (12), 1277–1285). Currently marketed drugs such as clonazepam and diazepam can relieve symptoms, but they also have side effects that are characteristic of the benzodiazepine class of drugs (that is, sedation and impairment of cognition and psychomotor performance). Nevertheless, anticonvulsants have been evaluated for the treatment of social phobia and have produced clinical benefit (Jefferson J W, Benzodiazepines and anticonvulsants for social phobia (social anxiety disorder), *J. Clin. Psychiatry,* 2001, 62 (Suppl. 1), 50–53; Connor K M, et. al., Social phobia: issues in assessment and management, *Epilepsia,* 1999, 40 (Suppl 6), S60–65, discussion S73–74).

Post Traumatic Stress Disorder (PTSD) is defined by the presence of a set of psychiatric symptoms triggered by a severely stressful event and is characterized by "re-experiencing" the traumatic event (eg, military combat, rape, child abuse, severe burns and witnesses to a peer suicide) along with decreased responsiveness and avoidance of current events associated with the trauma. The psychiatric symptoms are 3 core symptom clusters: intrusive thoughts (i.e. "re-experiencing" events, flashbacks, nightmares, etc.), avoidance behaviors and hyperarousal. Some of these core symptoms are clinically indistinguishable or highly similar to sensory seizures in epilepsy.

Acute psychological stress is the presumed immediate cause of PTSD, resulting in physiologic hyperarousal (startle reactions, intrusive thoughts, illusions, overgeneralized associations, sleep problems, nightmares, dreams about the precipitating event, impulsivity, difficulties in concentration, and hyper-alertness).

Clinical evidence supports that the flashbacks in PTSD represent an amalgam of abnormal neuronal firing along with the expression of a dynamically charged event (Brodsky L, Post traumatic stress disorder: an eclectic approach, *International Journal of Psychosomatics,* 1990, 37 (1–4), 89–95).

Anticonvulsants with a broad spectrum of activity most likely act to decrease the number and intensity of seizures and PTSD symptoms by regulating abnormal neuronal discharge patterns (Brodsky L, Post traumatic stress disorder: an eclectic approach, *International Journal of Psychosomatics,* 1990, 37 (1–4), 89–95). Based on this unique pathophysiology relevant to trauma-related alterations in arousal and memory, anticonvulsants are expected to prove effective in treating PTSD due to the anti-kindling/anti-sensitization and neurostabilizing properties of this class of drugs (Adamec R and Shallow T, Effects of baseline anxiety on response to kindling of the right medial amygdala, *Physiol. Behav.,* 2000, 70 (1/2), 67–80; Friedman M J, What might the psychobiology of posttraumatic stress disorder teach us about future approaches to pharmacotherapy? *J. Clin. Psychiatry,* 2000, 61(Suppl. 7), 44–51; Stam R, et. al., Long-lasting stress sensitisation, *Eur. J. Pharmacol.* 2000, 405 (1–3), 217–224; Southwick S M, Role of norepinephrine in the pathophysiology and treatment of posttraumatic stress disorder, *Biol. Psychiatry,* 1999, 46 (9), 1192–1204).

Indeed, several anticonvulsant drugs such as carbamazepine, valproate and lamotrigine all have shown efficacy in PTSD (Hertzberg M A, A preliminary study of lamotrigine for the treatment of positraumatic stress disorder, *Biological Psychiatry,* 1999, 45 (9),1226–9; Davidson J R, Biological therapies for posttraumatic stress disorder: an overview, *J. Clinical Psychiatry,* 1997, 58 (Suppl), 929–32; Friedman M J, Drug treatment for PTSD: Answers and questions, *Annals of the New York Academy of Sciences,* 1997 (June 21), 821359–71; Ford N, The use of anticonvulsants in posttraumatic stress disorder: case study and overview, *J. Traumatic Stress,* 1996, 9 (4), 857–63; Sutherland S M and Davidson J R, Pharmacotherapy for post-traumatic stress disorder, *Psychiatric Clinics of North America,* 1994, 17 (2), 409–23; Keck P E Jr., Valproate and carbamazepine in the treatment of panic and posttraumatic stress disorders, withdrawal states, and behavioral dyscontrol syndromes, *J. of Clinical Psychopharmacology,* 1992, 12 (1 Suppl), 36S–41S).

Clinical evidence further shows support for several anticonvulsant drugs (such as carbamazepine, divalproex sodium, gabapentin, lamotrigine, topiramate and vigabatrin) having efficacy in the treatment of PTSD symptoms (Berigan, T R., Holzgang A, Valproate As An Alternative In Post-Traumatic Stress: A Case Report, Military Medicine, 1995, 160(6):318; Berlant J. Topiramate In Chronic Civilian PTSD—An Open-Label Study of a Novel Treatment, International Society for Traumatic Stress Studies, Melbourne, Australia, 2000; Brannon N, Labbate L, Huber M, Gabapentin Treatment For Posttraumatic Stress Disorder, Canadian J. Psychiatry, 2000, 45(1):84; Brodsky L, Doerman A L, Palmer L S, Slade G F, Munasifi F A, Post Traumatic Stress Disorder: An Eclectic Approach, Int. J. Psychosomat, 1990, 37(1–4):89–95; Clark, R D, Divalproex In Postraumatic Stress Disorder: An Open-Label Clinical Trial, J. Trauma. Stress, 1999, 12(2):395–401; Fesler, F A, Valproate In Combat-Related Posttraumatic Stress Disorder, J. Clin. Psychiatry, 1991, 52(9):361–364; Hertzberg M A, Blutterfield M I, Feldman M E et al, A Preliminary Study of Lamotrigine for the treatment of Positraumatic Stress Disorder, Biol. Psychiatry, 1999, 45:1226–1229; Lipper S, Davidson J R T, Grady T A et al, Preliminary Study Of Carbamazepine In Posttraumatic Stress Disorder, Psychosomatics, 1986, 27(12):849–854; Looff D, Grimley P, Kuller F, Martin A, Schonfield L, Carbamazepine for PTSD, J. Am. Acad. Child Adolesc. Psychiatry, 1995, 34(6):703–704; MacLeod, A D, Vigabatrin and Posttraumatic Stress Disorder, J. Clin. Psychopharmacol, 1996, 16(2):190–191; Szymanski H V, Olympia J, Divalproex In Posttraumatic Stress Disorder, Am. J. Psychiatry, 1991, 148(8):1086–1087, Wolf M E, Alavi A, Mosnaim A D, Posttraumatic Stress Disorder In Vietnam Veterans: Clinical, Biol. Psychiatry, 1998, 23:642:644).

The lifetime prevalence of any anxiety disorder is 24.9%. This number represents 15 to 20% of all medical clinic patients. Only 27% of such individuals have received effective treatment (National Institute of Mental Health, 2001).

Substituted phenyl alkyl carbamate compounds have been described in U.S. Pat. No. 3,265,728 to Bossinger, et al (hereby incorporated by reference), as useful in treating the central nervous system, having tranquilization, sedation and muscle relaxation properties of the formula:

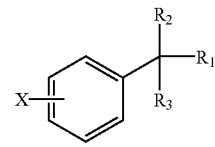

wherein $R_1$ is either carbamate or alkyl carbamate containing from 1 to 3 carbon atoms in the alkyl group; $R_2$ is either hydrogen, hydroxy, alkyl or hydroxy alkyl containing from 1 to 2 carbons; $R_3$ is either hydrogen or alkyl containing from 1 to 2 carbons; and X can be halogen, methyl, methoxy, phenyl, nitro or amino.

A method for inducing calming and muscle relaxation with carbamates has been described in U.S. Pat. No. 3,313,692 to Bossinger, et al (hereby incorporated by reference) by administering a compound of the formula:

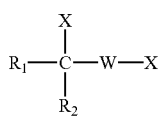

in which W represents an aliphatic radical containing less than 4 carbon atoms, wherein $R_1$ represents an aromatic radical, $R_2$ represents hydrogen or an alkyl radical containing less than 4 carbon atoms, and X represents hydrogen or hydroxy or alkoxy and alkyl radicals containing less than 4 carbon atoms or the radical:

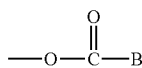

in which B represents an organic amine radical of the group consisting of heterocyclic, ureido and hydrazino radicals and the radical —$N(R_3)_2$ wherein $R_3$ represents hydrogen or an alkyl radical containing less than 4 carbon atoms.

Optically pure forms of halogen substituted 2-phenyl-1, 2-ethanediol monocarbamates and dicarbamates have also been described in U.S. Pat. No. 6,103,759 to Choi, et al (hereby incorporated by reference), as effective for treating and preventing central nervous system disorders including convulsions, epilepsy, stroke and muscle spasm; and as useful in the treatment of central nervous system diseases, particularly as anticonvulsants, antiepileptics, neuroprotective agents and centrally acting muscle relaxants, of the formulae:

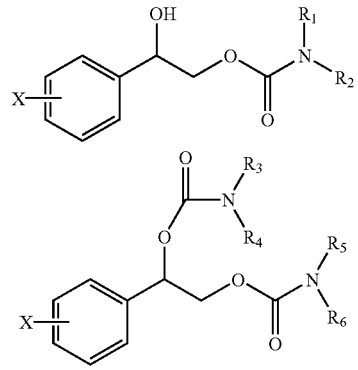

wherein one enantiomer predominates and wherein the phenyl ring is substituted at X with one to five halogen atoms selected from fluorine, chlorine, bromine or iodine atoms and $R_1$, $R_2$, $R_3$, $R_4$, $R_5$ and $R_6$ are each selected from hydrogen and straight or branched alkyl groups with one to four carbons optionally substituted with a phenyl group with substituents selected from the group consisting of hydrogen, halogen, alkyl, alkyloxy, amino, nitro and cyano. Pure enantiomeric forms and enantiomeric mixtures were described wherein one of the enantiomers predominates in the mixture for the compounds represented by the formulae above; preferably one of the enantiomers predominates to the extent of about 90% or greater; and, most preferably, about 98% or greater.

Halogen substituted 2-phenyl-1,2-ethanediol carbamate compounds of Formula (I) or Formula (II) have not been previously described as useful for preventing or treating anxiety disorders. Recent preclinical studies have revealed previously unrecognized pharmacological properties which suggest that a compound of Formula (I) or Formula (II) is useful in preventing or treating anxiety disorders. Therefore, it is an object of the present invention to teach a method for use of a compound of Formula (I) or Formula (II) in preventing or treating anxiety disorders.

SUMMARY OF THE INVENTION

The present invention is directed to a method for preventing or treating anxiety disorders comprising administering to a subject in need thereof a therapeutically effective amount of a compound selected from the group consisting of Formula (I) and Formula (II):

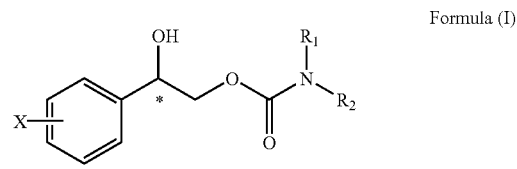

Formula (I)

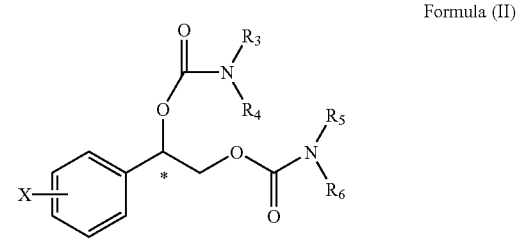

Formula (II)

wherein
phenyl is substituted at X with one to five halogen atoms selected from the group consisting of fluorine, chlorine, bromine and iodine; and,
$R_1$, $R_2$, $R_3$, $R_4$, $R_5$ and $R_6$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

Embodiments of the invention include a method for preventing or treating anxiety disorders comprising administering to a subject in need thereof a therapeutically effective amount of a pharmaceutical composition comprising a pharmaceutically acceptable carrier and a compound selected from the group consisting of Formula (I) and Formula (II).

Embodiments of the invention include the use of a compound selected from the group consisting of Formula (I) and Formula (II) for the preparation of a medicament for preventing or treating anxiety disorders in a subject in need thereof.

Embodiments of the method include the use of an enantiomer selected from the group consisting of Formula (I) and Formula (II) or enantiomeric mixture wherein one enantiomer selected from the group consisting of Formula (I) and Formula (II) predominates. For enantiomeric mixtures wherein one enantiomer selected from the group consisting of Formula (I) and Formula (II) predominates, preferably, one enantiomer selected from the group consisting of Formula (I) and Formula (II) predominates to the extent of about 90% or greater. More preferably, one enantiomer selected from the group consisting of Formula (I) and Formula (II) predominates to the extent of about 98% or greater.

DETAILED DESCRIPTION OF THE INVENTION

The present invention is directed to a method for preventing or treating anxiety disorders comprising administering to a subject in need thereof a therapeutically effective amount of a compound selected from the group consisting of Formula (I) and Formula (II):

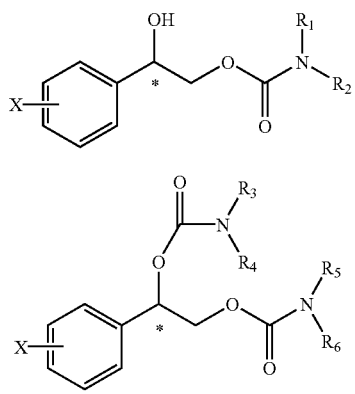

Formula (I)

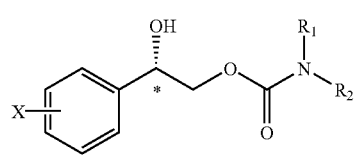

Formula (Ia)

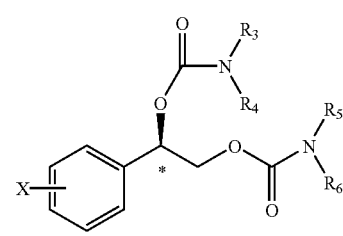

Formula (IIa)

wherein phenyl is substituted at X with one to five halogen atoms selected from the group consisting of fluorine, chlorine, bromine and iodine; and, $R_1$, $R_2$, $R_3$, $R_4$, $R_5$ and $R_6$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

The present method includes the use of a compound selected from the group consisting of Formula (I) and Formula (II) wherein X is chlorine; preferably, X is substituted at the ortho position of the phenyl ring.

The present method also includes the use of a compound selected from the group consisting of Formula (I) and Formula (II) wherein $R_1$, $R_2$, $R_3$, $R_4$, $R_5$ and $R_6$ are preferably selected from hydrogen.

An embodiment of the present method includes the use of an enantiomer selected from the group consisting of Formula (I) and Formula (II) or enantiomeric mixture wherein one enantiomer selected from the group consisting of Formula (I) and Formula (II) predominates wherein X is chlorine; preferably, X is substituted at the ortho position of the phenyl ring.

The present method also includes the use of an enantiomer selected from the group consisting of Formula (I) and Formula (II) or enantiomeric mixture wherein one enantiomer selected from the group consisting of Formula (I) and Formula (II) predominates wherein $R_1$, $R_2$, $R_3$, $R_4$, $R_5$ and $R_6$ are preferably selected from hydrogen.

For enantiomeric mixtures wherein one enantiomer selected from the group consisting of Formula (I) and Formula (II) predominates, preferably, an enantiomer selected from the group consisting of Formula (I) and Formula (II) predominates to the extent of about 90% or greater. More preferably, an enantiomer selected from the group consisting of Formula (I) and Formula (II) predominates to the extent of about 98% or greater.

An embodiment of the present method includes the use of an enantiomer selected from the group consisting of Formula (Ia) and Formula (IIa) or enantiomeric mixture wherein one enantiomer selected from the group consisting of Formula (Ia) and Formula (IIa) predominates:

wherein phenyl is substituted at X with one to five halogen atoms selected from the group consisting of fluorine, chlorine, bromine and iodine; and, $R_1$, $R_2$, $R_3$, $R_4$, $R_5$ and $R_6$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

The present method includes the use of an enantiomer selected from the group consisting of Formula (Ia) and Formula (IIa) or enantiomeric mixture wherein one enantiomer selected from the group consisting of Formula (Ia) and Formula (IIa) predominates wherein X is chlorine; preferably, X is substituted at the ortho position of the phenyl ring.

The present method also includes the use of an enantiomer selected from the group consisting of Formula (Ia) and Formula (IIa) or enantiomeric mixture wherein one enantiomer selected from the group consisting of Formula (Ia) and Formula (IIa) predominates wherein $R_1$, $R_2$, $R_3$, $R_4$, $R_5$ and $R_6$ are preferably selected from hydrogen.

For enantiomeric mixtures wherein one enantiomer selected from the group consisting of Formula (Ia) and Formula (IIa) predominates, preferably, an enantiomer selected from the group consisting of Formula (Ia) and Formula (IIa) predominates to the extent of about 90% or greater. More preferably, an enantiomer selected from the group consisting of Formula (Ia) and Formula (IIa) predominates to the extent of about 98% or greater.

An embodiment of the present method includes a method for preventing or treating anxiety disorders comprising administering to a subject in need thereof a therapeutically effective amount of an enantiomer selected from the group consisting of Formula (Ib) and Formula (IIb) or enantiomeric mixture wherein one enantiomer selected from the group consisting of Formula (Ib) and Formula (IIb) predominates:

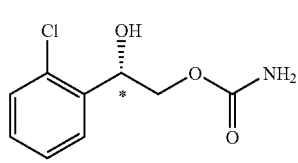

Formula (Ib)

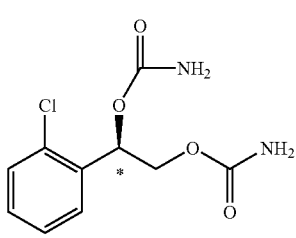

Formula (IIb)

For enantiomeric mixtures wherein one enantiomer selected from the group consisting of Formula (Ib) and Formula (IIb) predominates, preferably, an enantiomer selected from the group consisting of Formula (Ib) and Formula (IIb) predominates to the extent of about 90% or greater. More preferably, an enantiomer selected from the group consisting of Formula (Ib) and Formula (IIb) predominates to the extent of about 98% or greater.

Other crystal forms of the present invention may exist and as such are intended to be included in the present invention.

It is apparent to those skilled in the art that the compounds of the invention are present as racemates, enantiomers and enantiomeric mixtures thereof. A carbamate enantiomer selected from the group consisting of Formula (I), Formula (II), Formula (Ia), Formula (IIa), Formula (Ib) and Formula (IIb) contains an asymmetric chiral carbon atom at the benzylic position, which is the aliphatic carbon adjacent to the phenyl ring (represented by the asterisk in the structural formulae).

Compounds of the present invention may be prepared as described in the previously referenced Bossinger '728 patent (incorporated by reference), Bossinger '692 patent (incorporated by reference) and Choi '759 patent (incorporated by reference).

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The present invention contemplates a method for preventing or treating anxiety disorders in a subject in need thereof. Anxiety disorders include, but are not limited to, generalized anxiety disorders, panic disorders ((with or without agoraphobia) including anticipatory anxiety, recurrent sleep panic attacks (not nightmares) and distressing symptoms (eg, dyspnea, tachycardia, palpitations, headaches, dizziness, paresthesias, choking, smothering feeling, nausea and bloating) in association with feelings of impending doom (alarm response)), impulse control disorders (such as OCD, bulimia, episodic dyscontrol, trichotillomania, compulsive gambling and kleptomania), phobic disorders (including those disorders not due to impaired cognitive abilities, such as social phobia, global social phobia, specific social phobia, simple phobia, agoraphobia, apiphobia, tropophobia, astrapophobia, triskaidekaphobia, blennophobia, thalassophobia, claustrophobia, spheksophobia, cynophobia, sciophobia, decidophobia, eletrophobia, scholionophobia, eremophobia, pyrophobia, gamophobia, pnigerophobia, ophidiophobia, odynophobia, nyctophobia, ochlophobia, musophobia, keraunophobia, katagelophobia, kakorraphiophobia, hydrophobia, gynophobia, gatophobia, gephyrophobia, acrophobia or amathophobia), PTSD, dissociative states (including amnesia, somnambulism, dissociative identity disorder or depersonalization), presurgical anxiety states, postsurgical anxiety states or other medical or psychiatric induced anxiety conditions (including, but not limited to, anxiety resulting from traumatic brain injury, chronic pain disorders or other chronic disease conditions).

An example of the method of the present invention comprises administering to the subject a therapeutically effective amount of a compound selected from the group consisting of Formula (I) and Formula (II) in a pharmaceutical composition comprising a pharmaceutically acceptable carrier and a compound selected from the group consisting of Formula (I) and Formula (II). The method of the present invention also includes the use of a compound selected from the group consisting of Formula (I) and Formula (II) for the preparation of a medicament for preventing or treating anxiety disorders.

Another example of the method of the present invention comprises administering to the subject a therapeutically effective amount of a compound selected from the group consisting of Formula (I) and Formula (II) or a pharmaceutical composition thereof in combination with one or more agents useful in preventing or treating anxiety disorders.

A compound selected from the group consisting of Formula (I) and Formula (II) or pharmaceutical composition thereof may be administered by any conventional route of administration including, but not limited to, oral, pulmonary, intraperitoneal (ip), intravenous (iv), intramuscular (im), subcutaneous (sc), transdermal, buccal, nasal, sublingual, ocular, rectal and vaginal. In addition, administration directly to the nervous system may include, and are not limited to, intracerebral, intraventricular, intracerebroventricular, intrathecal, intracisternal, intraspinal or peri-spinal routes of administration by delivery via intracranial or intravertebral needles or catheters with or without pump devices. It will be readily apparent to those skilled in the art that any dose or frequency of administration that provides the therapeutic effect described herein is suitable for use in the present invention.

The therapeutically effective amount of a compound selected from the group consisting of Formula (I) and Formula (II) or pharmaceutical composition thereof may be from about 0.01 mg/Kg/dose to about 100 mg/Kg/dose. Preferably, the therapeutically effective amount may be from about 0.01 mg/Kg/dose to about 25 mg/Kg/dose. More preferably, the therapeutically effective amount may be from about 0.01 mg/Kg/dose to about 10 mg/Kg/dose. Most preferably, the therapeutically effective amount may be from about 0.01 mg/Kg/dose to about 5 mg/Kg/dose. Therefore, the therapeutically effective amount of the active ingredient contained per dosage unit (e.g., tablet, capsule, powder, injection, suppository, teaspoonful and the like) as described herein may be from about 1 mg/day to about 7000 mg/day for a subject, for example, having an average weight of 70 Kg.

The dosages, however, may be varied depending upon the requirement of the subjects (including factors associated with the particular subject being treated, including subject age, weight and diet, strength of the preparation, the advancement of the disease condition and the mode and time of administration) and the use of a particular compound of Formula (I) or Formula (II) or pharmaceutical composition thereof.

Optimal dosages to be administered may be readily determined by those skilled in the art and will result in the need to adjust the dose to an appropriate therapeutic level. The use of either daily administration or post-periodic dosing may be employed. Preferably, a compound of Formula (I) or Formula (II) or pharmaceutical composition thereof for treating anxiety disorders is administered orally or parenterally.

In accordance with the methods of the present invention, a compound of Formula (I) or Formula (II) or pharmaceutical composition thereof described herein may be administered separately, at different times during the course of therapy or concurrently in divided combination or single combination forms. Advantageously, a compound selected from the group consisting of Formula (I) and Formula (II) or pharmaceutical compositions thereof may be administered in a single daily dose or the total daily dosage may be administered via continuous delivery or in divided doses of two, three or four times daily. The instant invention is therefore to be understood as embracing all such methods and regimes of continuous, simultaneous or alternating treatment and the term "administering" is to be interpreted accordingly.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human, that is being sought by a researcher, veterinarian, medical doctor, or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

To prepare a pharmaceutical composition of the present invention, a compound of Formula (I) or Formula (II) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients,* published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded,* Volumes 1–3, edited by Lieberman et al; *Pharmaceutical Dosage Forms: Parenteral Medications,* Volumes 1–2, edited by Avis et al; and *Pharmaceutical Dosage Forms: Disperse Systems,* Volumes 1–2, edited by Lieberman et al; published by Marcel Dekker, Inc.

Preferably, a pharmaceutical composition is in a unit dosage form such as a tablet, pill, capsule, caplet, gelcap, lozenge, granule, powder, sterile parenteral solution or suspension, metered aerosol or liquid spray, drop, ampoule, autoinjector device or suppository for administration by oral, intranasal, sublingual, intraocular, transdermal, parenteral, rectal, vaginal, inhalation or insufflation means. Alternatively, the composition may be presented in a form suitable for once-weekly or once-monthly administration or may be adapted to provide a preparation for intramuscular injection.

In preparing a pharmaceutical composition having a solid dosage form for oral administration, such as a tablet, pill, capsule, caplet, gelcap, lozenge, granule or powder (each including immediate release, timed release and sustained release formulations), suitable carriers and additives include but are not limited to diluents, granulating agents, lubricants, binders, glidants, disintegrating agents and the like. If desired, tablets may be sugar coated, gelatin coated, film coated or enteric coated by standard techniques.

For preparing a solid dosage form, the principal active ingredient is mixed with a pharmaceutical carrier (e.g. conventional tableting ingredients such as diluents, binders, adhesives, disintegrants, lubricants, antiadherents and glidants). Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

In preparing a pharmaceutical composition having a liquid dosage form for oral, topical and parenteral administration, any of the usual pharmaceutical media or excipients may be employed. Thus, for liquid unit dosage forms, such as suspensions (i.e. colloids, emulsions and dispersions) and solutions, suitable carriers and additives include but are not limited to pharmaceutically acceptable wetting agents, dispersants, flocculation agents, thickeners, pH control agents (i.e. buffers), osmotic agents, coloring agents, flavors, fragrances, preservatives (i.e. to control microbial growth, etc.) and a liquid vehicle may be employed. Not all of the components listed above will be required for each liquid dosage form. The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles.

While the foregoing specification teaches the principles of the present invention, it will be understood that the practice of the invention encompasses all of the usual variations, adaptations and/or modifications as come within the scope of the following claims and their equivalents.

What is claimed is:

1. A method for preventing or treating anxiety disorders comprising administering to a subject in need thereof a therapeutically effective amount of a compound selected from the group consisting of Formula (I) and Formula (II):

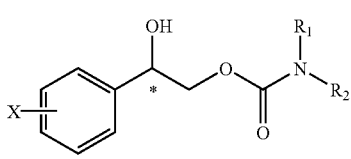

Formula (I)

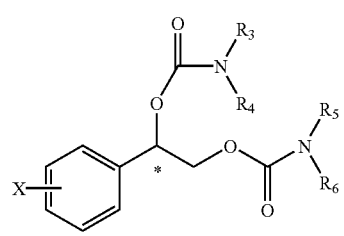

Formula (II)

wherein
  phenyl is substituted at X with one to five halogen atoms selected from the group consisting of fluorine, chlorine, bromine and iodine; and,
  $R_1$, $R_2$, $R_3$, $R_4$, $R_5$ and $R_6$ are independently selected from the group consisting of hydrogen and $C_1$–$C_4$ alkyl;
  wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

2. The method of claim 1 wherein X is chlorine.

3. The method of claim 1 wherein X is substituted at the ortho position of the phenyl ring.

4. The method of claim 1 wherein $R_1$, $R_2$, $R_3$, $R_4$, $R_5$ and $R_6$ are selected from hydrogen.

5. A method for preventing or treating anxiety disorders comprising administering to a subject in need thereof a therapeutically effective amount of an enantiomer selected from the group consisting of Formula (I) and Formula (II) or enantiomeric mixture wherein one enantiomer selected from the group consisting of Formula (I) and Formula (II) predominates:

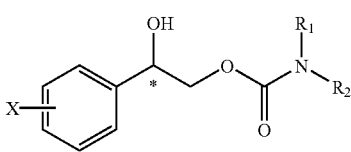

Formula (I)

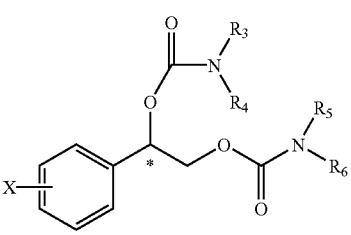

Formula (II)

wherein
  phenyl is substituted at X with one to five halogen atoms selected from the group consisting of fluorine, chlorine, bromine and iodine; and,
  $R_1$, $R_2$, $R_3$, $R_4$, $R_5$ and $R_6$ are independently selected from the group consisting of hydrogen and $C_1$–$C_4$ alkyl;
  wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano.

6. The method of claim 5 wherein X is chlorine.

7. The method of claim 5 wherein X is substituted at the ortho position of the phenyl ring.

8. The method of claim 5 wherein $R_1$, $R_2$, $R_3$, $R_4$, $R_5$ and $R_6$ are selected from hydrogen.

9. The method of claim 5 wherein one enantiomer selected from the group consisting of Formula (I) and Formula (II) predominates to the extent of about 90% or greater.

10. The method of claim 5 wherein one enantiomer selected from the group consisting of Formula (I) and Formula (II) predominates to the extent of about 98% or greater.

11. The method of claim 5 wherein the enantiomer selected from the group consisting of Formula (I) and Formula (II) is an enantiomer selected from the group consisting of Formula (Ia) and Formula (IIa):

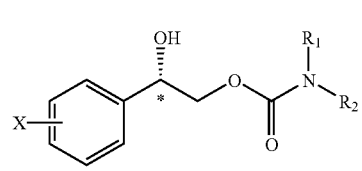

Formula (Ia)

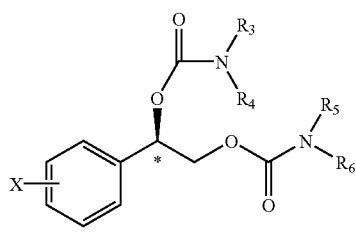

Formula (IIa)

wherein
  phenyl is substituted at X with one to five halogen atoms selected from the group consisting of fluorine, chlorine, bromine and iodine; and,
  $R_1$, $R_2$, $R_3$, $R_4$, $R_5$ and $R_6$ are independently selected from the group consisting of hydrogen and $C_1$–$C_4$ alkyl;
  wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano.

12. The method of claim 11 wherein X is chlorine.

13. The method of claim 11 wherein X is substituted at the ortho position of the phenyl ring.

14. The method of claim 11 wherein $R_1$, $R_2$, $R_3$, $R_4$, $R_5$ and $R_6$ are selected from hydrogen.

15. The method of claim 11 wherein one enantiomer selected from the group consisting of Formula (Ia) and Formula (IIa) predominates to the extent of about 90% or greater.

16. The method of claim 11 wherein one enantiomer selected from the group consisting of Formula (Ia) and Formula (IIa) predominates to the extent of about 98% or greater.

17. The method of claim 5 wherein the enantiomer selected from the group consisting of Formula (I) and Formula (II) is an enantiomer selected from the group consisting of Formula (Ib) and Formula (IIb):

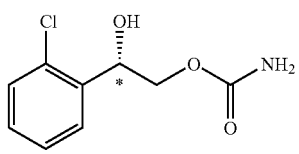

Formula (Ib)

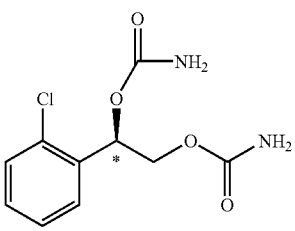

Formula (IIb)

18. The method of claim 17 wherein one enantiomer selected from the group consisting of Formula (Ib) and Formula (IIb) predominates to the extent of about 90% or greater.

19. The method of claim 17 wherein one enantiomer selected from the group consisting of Formula (Ib) and Formula (IIb) predominates to the extent of about 98% or greater.

20. The method as in claims 1 or 5 wherein the impulse Control disorder is selected from the group consisting of: intermittent explosive disorder (IED), kleptomania, obsessive compulsive disorder (OCD), pathological gambling, pyromania, trichotillomania, compulsive buying or shopping, repetitive self-mutilation, nonparaphilic sexual addictiions, severe nail biting, compulsive skin picking, episodic dyscontrol, personally disorders with impulsive features, attention deficit/hyperactivity disorder, eating disorders characterized by binge eating, and substance use disorders.

21. The method as in claim 1 or 5 wherein the therapeutically effective amount is from 0.001 mg/Kg/dose to about 100 mg/Kg/dose. Disorder is Obsessive-Compulsive Disorder (OCD).

22. The method of claim 21 wherein the anxiety disorder is positraumatic stress disorder.

* * * * *

UNITED STATES PATENT AND TRADEMARK OFFICE
CERTIFICATE OF CORRECTION

PATENT NO. : 7,078,436 B2
APPLICATION NO. : 10/081713
DATED : July 18, 2006
INVENTOR(S) : Plata-Salaman et al.

It is certified that error appears in the above-identified patent and that said Letters Patent is hereby corrected as shown below:

On the title page, item (54), delete "CARBAMATE COMPOUNDS FOR USE IN PREVENTING OR TREATING ANXIETY DISORDERS" and in place thereof insert --CARBAMATE COMPOUNDS FOR USE IN THE TREATMENT OF IMPULSE CONTROL DISORDERS--;

Column 12, line 64, delete "preventing or";

Column 12, line 64, delete "anxiety disorders" and in place thereof insert --an Impulse Control Disorder,--;

Column 12, line 65, delete "thereof" and in place thereof insert --of treatment,--;

Column 12, line 66, after the word "compound", insert --, or a pharmaceutically acceptable salt or ester thereof--;

Column 13, line 27, delete the parenthesis "(" before the word "wherein";

Column 13, line 30, delete the parenthesis ")" after the word "cyano";

Column 13, line 36, delete "preventing or";

Column 13, line 36, delete "anxiety disorders" and in place thereof insert the words --an Impulse Control Disorder--;

Column 13, line 37, delete "thereof" and in place thereof insert --of treatment--;

Column 13, line 38, after the word "enantiomer" insert--, or a pharmaceutically acceptable salt or ester thereof,--;

Column 13, line 67, after the word "phenyl" add a comma --,--;

Column 13, line 67, delete the parenthesis "(" before the word "wherein";

Column 13, line 69, after the word "wherein" add the word --the--;

UNITED STATES PATENT AND TRADEMARK OFFICE
CERTIFICATE OF CORRECTION

| | |
|---|---|
| PATENT NO. | : 7,078,436 B2 |
| APPLICATION NO. | : 10/081713 |
| DATED | : July 18, 2006 |
| INVENTOR(S) | : Plata-Salaman et al. |

It is certified that error appears in the above-identified patent and that said Letters Patent is hereby corrected as shown below:

Column 14, line 20, after the words "Formula (IIa)" add the words --or a pharmaceutically acceptable salt or ester thereof--;

Column 14, line 47, delete the parenthesis "(" before the word "wherein";

Column 14, , line 47, after the word "wherein" add the word --the--;

Column 14, line 69, after the words "Formula (IIa)" add the words --or a pharmaceutically acceptable salt or ester thereof--;

Column 16, line 5, after the word "method" insert a comma --,--;

Column 16, line 5, after the word "as" insert the word --claimed--;

Column 16, line 5, delete the word "impulse" and in place thereof insert --Impulse--;

Column 16, line 12, delete the word "personally" and in place thereof insert --personality--;

Column 16, line 16, after the word "method" insert a comma --,--;

Column 16, line 16, after the word "as" insert the word --claimed--;

Column 16, line 16, delete the numerals and words "1 or 5" and in place thereof insert the numeral --20--;

Column 16, lines 16 to 18, delete the words "therapeutically effective amount is from 0.001 mg/Kg/dose to about 100 mg/Kg/dose" and in place thereof insert the words --Impulse Control--;

UNITED STATES PATENT AND TRADEMARK OFFICE
CERTIFICATE OF CORRECTION

PATENT NO. : 7,078,436 B2
APPLICATION NO. : 10/081713
DATED : July 18, 2006
INVENTOR(S) : Plata-Salaman et al.

It is certified that error appears in the above-identified patent and that said Letters Patent is hereby corrected as shown below:

Column 16, line 20, delete the words and numerals "of claim 21" and in place thereof insert the words and numerals --as in claims 1 or 5--;

Column 16, lines 20 to 21, delete the words "anxiety disorder is postraumatic stress disorder" and in place thereof insert the words --therapeutically effective amount is from about 0.01 mg/Kg/dose to about 100 mg/Kg/dose--.

Signed and Sealed this

Twenty-fourth Day of June, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,078,436 B2 | Page 1 of 3 |
| APPLICATION NO. | : 10/081713 | |
| DATED | : July 18, 2006 | |
| INVENTOR(S) | : Plata-Salaman et al. | |

It is certified that error appears in the above-identified patent and that said Letters Patent is hereby corrected as shown below:

On the title page, item (54) and Column 1, lines 1-3, delete "CARBAMATE COMPOUNDS FOR USE IN PREVENTING OR TREATING ANXIETY DISORDERS" and in place thereof insert --CARBAMATE COMPOUNDS FOR USE IN THE TREATMENT OF IMPULSE CONTROL DISORDERS--;

Column 12, line 64, delete "preventing or";

Column 12, line 64, delete "anxiety disorders" and in place thereof insert --an Impulse Control Disorder,--;

Column 12, line 65, delete "thereof" and in place thereof insert --of treatment,--;

Column 12, line 66, after the word "compound", insert --, or a pharmaceutically acceptable salt or ester thereof--;

Column 13, line 27, delete the parenthesis "(" before the word "wherein";

Column 13, line 30, delete the parenthesis ")" after the word "cyano";

Column 13, line 36, delete "preventing or";

Column 13, line 36, delete "anxiety disorders" and in place thereof insert the words --an Impulse Control Disorder--;

Column 13, line 37, delete "thereof" and in place thereof insert --of treatment--;

Column 13, line 38, after the word "enantiomer" insert--, or a pharmaceutically acceptable salt or ester thereof,--;

Column 13, line 67, after the word "phenyl" add a comma --,--;

Column 13, line 67, delete the parenthesis "(" before the word "wherein";

Column 13, line 69, after the word "wherein" add the word --the--;

UNITED STATES PATENT AND TRADEMARK OFFICE
CERTIFICATE OF CORRECTION

PATENT NO. : 7,078,436 B2
APPLICATION NO. : 10/081713
DATED : July 18, 2006
INVENTOR(S) : Plata-Salaman et al.

It is certified that error appears in the above-identified patent and that said Letters Patent is hereby corrected as shown below:

Column 14, line 20, after the words "Formula (IIa)" add the words --or a pharmaceutically acceptable salt or ester thereof--;

Column 14, line 47, delete the parenthesis "(" before the word "wherein";

Column 14, , line 47, after the word "wherein" add the word --the--;

Column 14, line 69, after the words "Formula (IIa)" add the words --or a pharmaceutically acceptable salt or ester thereof--;

Column 16, line 5, after the word "method" insert a comma --,--;

Column 16, line 5, after the word "as" insert the word --claimed--;

Column 16, line 5, delete the word "impulse" and in place thereof insert --Impulse--;

Column 16, line 12, delete the word "personally" and in place thereof insert --personality--;

Column 16, line 16, after the word "method" insert a comma --,--;

Column 16, line 16, after the word "as" insert the word --claimed--;

Column 16, line 16, delete the numerals and words "1 or 5" and in place thereof insert the numeral --20--;

Column 16, lines 16 to 18, delete the words "therapeutically effective amount is from 0.001 mg/Kg/dose to about 100 mg/Kg/dose" and in place thereof insert the words --Impulse Control--;

UNITED STATES PATENT AND TRADEMARK OFFICE
CERTIFICATE OF CORRECTION

PATENT NO. : 7,078,436 B2
APPLICATION NO. : 10/081713
DATED : July 18, 2006
INVENTOR(S) : Plata-Salaman et al.

It is certified that error appears in the above-identified patent and that said Letters Patent is hereby corrected as shown below:

Column 16, line 20, delete the words and numerals "of claim 21" and in place thereof insert the words and numerals --as in claims 1 or 5--;

Column 16, lines 20 to 21, delete the words "anxiety disorder is postraumatic stress disorder" and in place thereof insert the words --therapeutically effective amount is from about 0.01 mg/Kg/dose to about 100 mg/Kg/dose--.

This certificate supersedes the Certificate of Correction issued June 24, 2008.

Signed and Sealed this

Twenty-second Day of July, 2008

JON W. DUDAS
*Director of the United States Patent and Trademark Office*